United States Patent [19]

Hadfield et al.

[11] Patent Number: 4,960,713

[45] Date of Patent: * Oct. 2, 1990

[54] DIAGNOSTIC TEST METHODS

[75] Inventors: Susan G. Hadfield; Franklin E. A. Norrington, both of Beckenham, England

[73] Assignee: Burroughs Wellcome Co., Research Triangle Park, N.C.

[*] Notice: The portion of the term of this patent subsequent to May 17, 2005 has been disclaimed.

[21] Appl. No.: 160,148

[22] Filed: Feb. 25, 1988

Related U.S. Application Data

[62] Division of Ser. No. 769,597, Aug. 26, 1985, Pat. No. 4,475,075.

[30] Foreign Application Priority Data

Sep. 6, 1984 [GB] United Kingdom ............ 22512
Jul. 10, 1985 [GB] United Kingdom ............ 17477

[51] Int. Cl.⁵ .............. G01N 33/53; G01N 33/545; G01N 33/577
[52] U.S. Cl. .............. 436/523; 422/61; 436/531; 436/533; 436/534; 436/808
[58] Field of Search ........... 436/523, 533, 534, 808, 436/531; 422/61

[56] References Cited

U.S. PATENT DOCUMENTS

| | | |
|---|---|---|
| 3,088,875 | 5/1963 | Fisk . |
| 4,115,535 | 9/1978 | Giaever . |
| 4,140,662 | 2/1979 | Reckel et al. . |
| 4,315,907 | 2/1982 | Fridlander et al. ......... 435/7 X |
| 4,342,739 | 8/1982 | Kakimi et al. . |
| 4,373,932 | 2/1983 | Gribnau et al. .......... 435/7 X |
| 4,376,110 | 3/1983 | David et al. ............ 435/7 X |
| 4,419,453 | 12/1983 | Dorman et al. ........... 436/534 |
| 4,436,826 | 3/1984 | Wang ................. 436/526 |
| 4,454,233 | 6/1984 | Wang ................. 436/525 |
| 4,511,662 | 4/1985 | Baran et al. ............ 436/513 |
| 4,554,257 | 11/1985 | Aladjam et al. ........... 436/519 |
| 4,639,419 | 1/1987 | Olson et al. ............ 435/5 |
| 4,745,075 | 5/1988 | Hadfield et al. ........... 436/523 |

FOREIGN PATENT DOCUMENTS

| | | |
|---|---|---|
| 0032270 | 7/1981 | European Pat. Off. . |
| 0070527 | 1/1983 | European Pat. Off. . |
| 1561042 | 2/1980 | United Kingdom . |
| 2086041 | 5/1982 | United Kingdom . |

OTHER PUBLICATIONS

Baran et al., American J. Clinical Pathology, vol. 83, No. 2, (2/1985), pp. 182-189.
Doskeland et al., J. Clinical Microbiology, vol. 11, No. 4, (4/1980), pp. 380-384.
Smith et al., J. Clinical Microbiology, vol. 20, No. 5, (11/1984),pp. 981-984.
Bio-Rad Quantigen Product Brochure Bulletin 4025, (Mar. 1984).
Hechemy et al., Laboratory Management (Jun. 1986), pp. 27-40.
Meridian Diagnostics, Inc., Meritec-Strep ™ Product Brochure (1982).
Pharmacia Diagnostics Phadebact ®Streptococcus Test Product Brochure (Mar. 1981).

Primary Examiner—Robert J. Warden
Assistant Examiner—Jill Johnston
Attorney, Agent, or Firm—Donald Brown

[57] ABSTRACT

Agglutination assays, particularly latex agglutination assays, for simultaneous testing for a multiplicity of ligands. The reagents for use in the assays comprise two or more insoluble colored substances, each substance being adapted to form a distinctively colored agglutinate in the presence of a specific ligand or specific group of ligands.

24 Claims, No Drawings

DIAGNOSTIC TEST METHODS

This application is a divisional of application Ser. No. 769,597, filed on Aug. 26, 1985, now U.S. Pat. No. 4,475,075.

The present invention relates to an agglutination test for the detection of a ligand and to a diagnostic test kit for use in the detection of a ligand.

Diagnostic test methods based upon the agglutination of immunogens and antibodies, wherein either the immunogen or the antibody is attached to a solid phase, are well known in the field of immunodiagnostic reagents. For example, U.S. Pat. No. 3,088,875 describes a technique wherein plastic microspheres coated with antigen are mixed with a test sample such that when the sample contains antibodies to the antigens, the antibodies attach themselves to the antigen thereby causing visible agglutination or aggregation of the microspheres.

Coloured solid phases or particles have been used to aid visualisation of the agglutination process. For example, there are marketed test kits for the grouping of Beta Haemolytic Streptococci which include reagents in which the solid phase is a suspension of killed red-dyed or blue-dyed *Staphylococcus aureus* cells. There is also marketed a test kit containing four separate reagents, each containing a different colour of latex particle, for the detection and grouping of streptococci A, B, C and G. By assigning a specific colour to each test reagent any confusion which could be caused by e.g. incorrect labelling is avoided.

U.S. Pat. No. 4,419,453 describes a latex agglutination test in which the test reagent comprises antigen or antibody coated latex particles of one colour and a water-soluble non-latex polymer particle absorbing dye of a different colour. When agglutination takes place, the contrast between the colour of the aggregate and the background colour of the solution assists visualisation.

A diagnostic technique such as a latex agglutination test is generally used to reinforce an initial diagnosis based upon the clinical symptoms exhibited by a patient suffering from a particular disease. In cases where a disease is characterised by very distinctive symptoms, confirmation of the presence of a causative agent (e.g. bacteria or viruses) could involve relatively few tests. However, with diseases in which the symptoms could be ascribed to any one of a large number of causative agents, it will be apparent that much time and effort could be expended in performing a test against each of the possible causative agents and that the size of sample required from the patient could be considerable. This could be a serious problem in instances (e.g. when the test fluid is neonatal cerebro-spinal fluid (CSF)) where it is only possible to take small samples of biological material from the patient.

Heterogeneous specific binding assays are known wherein a plurality of ligands can be determined simultaneously in the single test sample thereby reducing the number of tests needed. Such combined assays are considered (see UK Patent application No. 2 034 466A) to be of particular advantage where the assays are of a screening nature, for example in the diagnosis of immunity to viruses and other antigens responsible for congenital malformations such as Rubella, Cytomegalovirus and Herpes simplex virus. A combined assay could indicate the patient's immunity against two or more of these antigens, in a single test by detecting the presence of antibodies to each of the antigens. UK Patent application No. 2034466A describes such an assay wherein the ligands are differentiated by the use of a number of differentially separable solid phases. Such solid phases can be, for example, a plate coated with one immunologically active substance in a container the walls of which are coated with another immunologically active material. Following the appropriate series of immunochemical reactions the ligand-immunochemical complexes can be separated simply by removing the plate from the container.

Further combined assays are known where, for example, different specific binding substances are linked to particles of different size (UK Patent No. 1561042), or where microscopically distinguishable rosettes are formed between ligand and binding substance (UK Patent Application No. 2122345), and where each specific binding substance is linked to a latex particle distinguishably labelled with a radioactive substance or an element detectable by e.g. X-ray fluorescence spectroscopy (U.S. Pat. No. 4,436,826).

The abovementioned methods for determining more than one ligand suffer from the disadvantages of either requiring complex instrumentation or requiring mechanical separation of the various types of solid phase or of being inapplicable as a general means of detecting immunogens, antibodies and other specifically bindable substances. The above methods in general also take longer to perform than agglutination tests. Furthermore, those assays which employ radioactive or heavy metal elements have the additional disadvantage of requiring special safety and waste disposal procedures. It is thus apparent that there exists a need for a technique which is rapid, safe, simple and broadly applicable and which can significantly reduce the number of tests required to identify the causative agent of an infection or disease thereby reducing the volumes of biological material required to be taken from a patient in order to carry out those tests. There has now been discovered such a technique.

Accordingly, the present invention provides in a first aspect an agglutination method for the detection of a ligand or group of ligands in a medium, which method comprises mixing the medium with a reagent containing two or more insoluble coloured substances, each substance being adapted to form a distinctively coloured agglutinate in the presence of a specific ligand or specific group of ligands, and determining the presence of the ligand by establishing whether or not the distinctively coloured agglutinate has formed.

By distinctively coloured, it is meant that the colour of the agglutinate formed in the presence of one particular ligand or group of ligands is different from that of any agglutinates formed in the presence of other ligands or groups of ligands and that it is distinguishable from the background colour i.e. the colour due to any unagglutinated particles. The distinctive colour of the agglutinate is due to each insoluble substance being different in colour from the other insoluble substances. The agglutinate is preferably visible to the naked eye.

The above agglutination test is carried out in an appropriate solvent in which the coloured substances are insoluble, preferably an aqueous solvent.

The term ligand, as used in the context of the present invention includes antigens, haptens, monoclonal and polyclonal antibodies and other substances capable of being bound by a specific binding substance. Such other substances include avidin, biotin, lectins, carbohydrates specifically bindable to lectins, Protein A and the FC fragment of IgG.

The medium may be a biological sample such as a body fluid taken from an animal, human or otherwise, or it may be any other type of medium in which a ligand may be found. Such media can include for example culture broths, suspensions from liquid or solid growth media, culture supernatants, tissue culture supernatants, enzyme or chemically extracted material from bacteria and viruses (e.g. Lancefield extracts for serological grouping of Streptococci), foodstuffs or environmental samples (e.g. water samples from the public supply).

Biological samples which can be taken from animals include cerebrospinal fluid, blood, urine, sputum, tissue extracts, sweat, tears, secretions, faeces, mucus and synovial fluid.

The above list is not intended to be exhaustive and the skilled man will appreciate that other types of biological sample may be taken and tested by the method of present invention.

The insoluble coloured substance is adapted to form a distinctively coloured agglutinate in the presence of a specific ligand or group of ligands by being linked to, or containing, a specific binding substance or group of specific binding substances capable of binding to the ligand or group of ligands. The specific binding substance can be an immunological counterpart to the ligand; thus if the ligand is an antibody, the specific binding substance will be the antigen to that antibody and vice versa. It can also be a substance such as avidin, biotin, a lectin, a carbohydrate specifically bindable to a lectin, Protein A and the FC fragment of IgG.

The insoluble coloured substance is preferably a particle of microscopic size. Particulate materials which are coloured, or can be dyed, and are suitable for use in the abovementioned assay include non-viable bacterial cells, alginate particles, Sepharose beads, silica, alumina, erythrocytes, polymer latexes such as polystyrene latexes, styrene-glycidyl methacrylate latex and other polymer latexes such those described in U.S. Pat. No. 4,419,453. Coloured particles may be prepared or dyed according to standard methods, see for example U.S. Pat. No. 4,419,453 and German Patent Application DT-3000-483, or they may be purchased from an appropriate source. Particularly suitable colours include red, yellow, blue, green, black, cyan, magenta and white.

The specific binding substance is linked to the particle by adsorption, by chemical coupling, by incorporation into the particle or by any other method known in the art.

Adsorbing or coating the binding substance onto the particles is typically achieved by incubation of the particles with a suitably buffered solution of the binding substance. Chemical coupling can be achieved for example by the method described in U.S. Pat. No. 4,436,826 wherein a carbodiimide coupling reagent is employed. A similar coupling process is also described in U.S. Pat. No. 4,140,662.

The present invention is especially useful for the detection of bacterial, viral or parasitic infections and the identification of antigen or antibody in biological fluids. It is particularly useful in the analysis of spinal fluid (e.g. neonatal spinal fluid) for such species as *Haemophilus influenzae*, *Neisseria meningitidis* and *Streptococcus pneumoniae*. An important advantage of the present invention is the reduced volume of spinal fluid required for analysis compared with more conventional agglutination test methods.

The present invention is also useful for the identification of serologically distinct strains e.g. Streptococcal serogroups A, B, C, D, F and G, Salmonella O or H antigens and Meningococci serogroups A, B, C, Y, 29E and Z.

It will be appreciated that each insoluble coloured substance can be adapted to form an agglutinate in the presence of a single ligand by containing or being linked to a single specific binding substance. A method, and a reagent employing an insoluble coloured substance so adapted represents one preferred aspect of the invention.

In one particularly preferred embodiment of the present invention, the reagent comprises a suspension of antibody coated latex particles of three colours, the colour of each particle indicating the particular specific antibody with which it is coated. The overall appearance of the reagent before reaction is a dull or greyish colour. Following admixture of the reagent with a medium containing an antigen capable of being bound by one of the specific antibodies, the said antigen will react with the appropriate antibody causing formation of an agglutinate. It will be apparent from the colour of the agglutinate which antibody has taken part in the reaction and hence the identity of the antigen will be revealed. Visualisation of the agglutinate is enhanced by the colour contrast with the background colour provided by the non-agglutinated particles. Thus for example, when the reagent contains red, blue and green particles, if agglutination of the red particles has occurred, the background is a contrasting turquoise. If blue particles have agglutinated, they appear against an orange or yellow coloured background and if the green particles are agglutinated, the background is a purplish colour.

Non-specific interactions, such as those due to the presence of interfering substances such as Rheumatoid Factor (RF) or Protein A (found on most *S. aureus* bacteria) and Protein A-like substances (found on some streptococci) will tend to show up as dark clumps on a lighter background of similar hue.

Although the above preferred embodiment is illustrated by reference to the detection of a single antigen, the present invention can be used to detect simultaneously more than one antigen. Thus for example in the three colour system described above, the simultaneous presence of two antigens could be demonstrated by e.g. the formation of an agglutinate of blue and green particles against a red background or by an agglutinate of green and red particles against a blue background. It will readily be appreciated that in such instances, the background colour is particularly useful in enabling the outcome of the immunochemical reaction to be interpreted.

It will also be appreciated that each insoluble coloured substance can be adapted to form an agglutinate in the presence of a specific group of ligands. For example each substance could contain, or be linked to, antibodies to two or more bacterial or viral antigens.

Thus in another embodiment of the present invention, there is provided an agglutination method substantially as described hereinabove but wherein the reagent contains at least two and preferably at least three insoluble coloured substances, at least one and preferably at least two of which each contain, or are linked to, at least two specific binding substances. The individual specific binding substances making up the group can be associated with particular insoluble coloured substances, or certain of the binding substances can be common to two or more of the insoluble coloured substances.

In the former case it is evident that the agglutination method represents a means of "narrowing down" a range of possible infecting agents to a small group of such agents, further tests then being required to identify precisely the infecting agent. Such a method is envisaged as being particularly useful in the diagnosis of diseases e.g. bacterial or viral diseases, in which the symptoms are typical of any of a very large number of possible infecting agents.

An example of the latter case could be a reagent comprising, for example, red, blue and green latex particles, the red particles being coated with antibodies to antigens A and B, the blue particles being coated with antibodies to antigens B and C and the green particles being coated with antibodies to antigens A and C. Addition of a test sample containing one antigen to which the reagent was sensitised would result in the co-agglutination of particles of two colours, identification of the antigen subsequently being made most readily on the basis of the background colour. Thus, for example, if the test sample contained antigen A, red and green particles would co-agglutinate giving rise to a readily recognisable blue background.

It will be recognised by the skilled man that when one or more of the specific binding substances is or are common to more than one insoluble coloured substance, by employing an appropriate permutation of insoluble coloured substances and specific binding substances, it is possible to detect specifically up to $2^n - 2$ ligands where n is the number of insoluble coloured substances employed. Thus a three colour reagent could be used to detect and identify six ligands. For example such a reagent could comprise red, green and blue particles, the red particles being sensitised to ligands A, C and D, the green particles to ligands B, E and D and the blue particles to ligands C, F and E.

The outcome of adding each of the ligands A-F is shown below.

| Ligand | Colour of Agglutinate (Agglutinated Particles) | Background Colour (Non-agglutinated colours) |
|---|---|---|
| A | RED | BLUE + GREEN |
| B | GREEN | BLUE + RED |
| C | RED + BLUE | GREEN |
| D | RED + GREEN | BLUE |
| E | BLUE + GREEN | RED |
| F | BLUE | RED + GREEN |

Thus the colour of the agglutinate would be most useful in detecting and identifying ligands A, B and F whilst the colour of the background would be most useful in the detection and identification of ligands C, D and E.

In each of the above-mentioned methods according to the present invention, it is desirable in certain instances to pre-treat the medium before testing; such methods of pre-treatment include treatment with acids, or enzyme extractions, and also filtering, centrifuging, diluting, concentrating and heating. By heating, for example, it is possible to deactivate or significantly reduce the activity of the abovementioned interfering substances.

In conventional agglutination techniques, it is usual to employ a control latex which is a suspension of latex particles coated with the immunoglobulin fraction (hereinafter referred to as the control antiserum) of an animal that has not been inoculated with the antigen under test, or a monoclonal antibody of the same class as that used on the test latex but having a different specificity. Agglutination of the control latex in the presence of a test sample indicates a non-specific interaction.

The drawback to using a control latex reagent in conventional procedures is that at least one additional aliquot of biological test fluid is required for each test or series of tests, this additional aliquot subsequently yielding no useful information as to the identity of the infecting agent.

There has now been discovered a technique in which the disadvantageous requirement for a separate control latex reagent has been overcome. Accordingly, in another aspect of the present invention there is provided a direct agglutination test for the present of a ligand in a medium which method comprises; mixing the medium with a reagent containing (i) an antibody bindable to the ligand, said antibody being insolubilised by attachment to a particle of a first colour and (ii) a particle of a second colour coated with control serum; observing whether agglutination occurs and determining the colour of the agglutination.

For example, in a typical test procedure, the test sample is mixed with a reagent containing blue latex particles coated with antibody to the antigen to be detected and red latex particles coated with a control serum. If the suspected antigen is present and there are no non-specific interactions, a blue agglutination will be formed against a red background. If non-specific interactions do occur, both red and blue particles will agglutinate giving rise to clumps of a purplish colour. It will be apparent to the skilled man that although red and blue particles are described by way of example, any two contrasting colours could be used in place thereof.

In a further aspect, the present invention provides a kit for use in the detection of a ligand, which kit comprises a reagent containing two or more insoluble coloured substances, each substance being adapted to bind to a specific ligand and having its own specific colour.

In yet another aspect, there is provided a kit for use in the detection of a ligand comprising a reagent containing (i) an antibody bindable to the ligand, said antibody being insolubilised by attachment to a particle of a first colour and (ii) a particle of a second colour coated with a control serum.

There is also provided a kit comprising a reagent containing two or more insoluble coloured substances, at least one and preferably at least two of which each contain, or are linked to, at least two specific binding substances.

Other items which can usefully be included in the abovementioned kits include spotting cards, mixing sticks, a positive control antigen for each antigen being tested, negative control "antigen" (e.g. saline solution) and a set of instructions for use of the test kit.

The present invention will now be illustrated by means of examples. The examples should not be construed as imposing a limitation on the scope of the invention.

EXAMPLE 1

Preparation of Sensitised Latex

I. Preparation of antibody

Immunoglobulin G was obtained partially purified from immune rabbit sera by treatment with octanoic acid (BDH Chemicals Ltd.) using the method of Steinbuch and Audran (*Arch. Biochem. and Biophys,* 134, 279–284, 1969).

II. Binding of antibody to coloured latex

To 5.0 mg of coloured latex (Estapor, K58, 0.2μ, polystyrene, black, red, blue, yellow or green, Rhone-Poulenc. Fr. Pat. Appl. No. 82 00485 Eur. Pat. Appl. No. 85016) was added 600 μg. of antibody in 1 ml. of glycine saline pH 8.2 (0.1M glycine in 0.85% NaCl, pH adjusted to 8.2 with NaOH). Latex and antibody were heated at 56° C. for 30 mins. After cooling to room temperature bovine albumin (Miles Laboratories Ltd.) was added to give a 1% (w/v) concentration.

III. Preparation of polyvalent latex

Three different coloured latexes each one sensitised with antibody of a different specificity e.g. red latex coated with antibody to Salmonella serogroup A, blue latex coated with antibody to serogroup B and green latex coated with antibody to serogroup C, were mixed together in equal proportions. The resultant latex was brown in colour.

EXAMPLE 2

Use of the polyvalent Latex

Latex agglutination tests were performed on white cards (Syfacard -R, Wellcome Dagnostics Ltd.). Equal volumes of the test sample and the polyvalent latex (usually 20 μl) were mixed together on a circle, diameter 2 cm., on the white card. The card was rocked for 3 mins. after which the sample was examined for agglutination. The colour of the agglutinate was identified e.g. red, blue or green and at the same time the colour of the unagglutinated latex changed from brown to a combination of the colours of the two particles remaining unagglutinated in suspension.

(a) Bacterial colony identification

A single colony of bacteria was removed from a solid growth medium and emulsified in 200 μl of 0.85% saline. The bacterial suspensions were mixed with the polyvalent latex as described above.

| ANTIGEN | RESULT |
| --- | --- |
| 1. Saline only. | Brown homogenous solution. |
| 2. Salmonella Serogroup A eg. *S. paratyphi A* | red agglutinate in a turquoise solution |
| 3. Salmonella Serogroup B eg. *S. typhimurium* | blue agglutinate in an orange solution. |
| 4. Salmonella Serogroup C eg. *S. newport* | green agglutinate in a purple Solution. |

(b) Antigen detection in biological fluids

Spinal fluid taken from a patient with meningitis was tested, as described above, against the Salmonella polyvalent latex. Agglutination of the red latex particles occurred indicating the presence of antigen from Salmonella serogroup B organisms in the spinal fluid. Spinal fluid from an uninfected person did not cause agglutination of the latex.

We claim:

1. A method of testing for the presence of three ligands in an aqueous liquid medium comprising the steps of:

A. mixing a sample of the said medium with a reagent comprising a mixture of polymer latex particles collectively of three colors, the particles of the first of said three colors having attached thereto antibody selectively bindable to the first of said three ligands, the particles of the second of said three colors having attached thereto antibody selectively bindable to the second of said three ligands and the particles of the third of said three colors having attached therto antibody selectively bindable to the third of said three colors, whereby the presence of the first of said three ligands in the sample is indicated by the selective agglutination of the particles of the first of said three colors having attached thereto the antibody selectively bindable to the first of said three ligands, the presence of the second of said three ligands in the sample is indicated by the selective agglutination of the particles of the second of said three colors having attached thereto the antibody selectively bindable to the second of said three ligands and the presence of the third of said three ligands in the sample is indicated by the selective agglutination of the particles of the third of said three colors having attached thereto the antibody selectively bindable to the third of said three ligands;

B. after an appropriate period of time, inspecting the mixture resulting from step A; and C. determining the presence of three ligands from the appearance of said mixture.

2. The method of claim 1 wherein, in the reagent employed in step A., the antibody attached to the particles of at least one of said three colours is polyclonal.

3. The method of claim 2 wherein the polyclonal antibody was raised in a rabbit.

4. The method of claim 1 wherein, in the reagent employed in step A., the antibody attached to the particles of at least one of said three colours is monoclonal.

5. The method of claim 1 wherein all of the particles are of polystyrene latex.

6. The method of claim 1 wherein at least one of said three ligands is a viral antigen.

7. The method of claim 1 wherein at least one of said three ligands is a bacterial antigen.

8. The method of claim 1 wherein at least one of said three ligands is an antigen characteristic of Haemophilus organisms.

9. The method of claim 1 wherein at least one of said three ligands is an antigen characteristic of Neisseria organisms.

10. The method of claim 1 wherein at least one of said three ligands is an antigen characteristic of Salmonella organisms.

11. The method of claim 1 wherein at least one of said three ligands is an antigen characteristic of Streptococcus organisms.

12. The method of claim 1 wherein at least one of said three ligands is an antigen characteristic of Streptococcus organisms of serogroup A.

13. A test reagent for determining the presence of three ligands in a sample of an aqueous liquid medium which comprises a mixture of polymer latex particles collectively of three colors, the particles of the first of said three colors having attached thereto antibody selectively bindable to the first of said three ligands, the particles of the second of said three colors having attached thereto antibody selectively bindable to the second of said three ligands and the particles of the third of said three colors having attached thereto antibody selectively bindable to the third of said three ligands, whereby the presence of the first of said three ligands in the sample is indicated by the selective agglutination of the particles having attached thereto the antibody selectively bindable to the first of said three ligands, the presence of the second of said three ligands in the sample is indicated by the selective agglutination of the particles having attached thereto the antibody selectively bindable to the second of said three ligands and the presence of the third of said three ligands in the sample is indicated by the selective agglutination of the particles having attached thereto the antibody selectively bindable to the third of said three ligands.

14. The reagent of claim 13 wherein the antibody attached to the particles of at least one of said three colour is polyclonal.

15. The reagent of claim 14 wherein the polyclonal antibody was raised in a rabbit.

16. The reagent of claim 13 wherein the antibody attached to the particles of at least one of said three colour is monoclonal.

17. The reagent of claim 13 wherein all of the particles are of polystyrene latex.

18. The reagent of claim 13 wherein at least one of said three ligands is a viral antigen.

19. The reagent of claim 13 wherein at least one of said three ligands is a bacterial antigen.

20. The reagent of claim 13 wherein at least one of said three ligands is an antigen characteristic of Haemophilus organisms.

21. The reagent of claim 13 wherein at least one of said three ligands is an antigen characteristic of Neisseria organisms.

22. The reagent of claim 13 wherein at least one of said three ligands is an antigen characteristic of Salmonella organisms.

23. The reagent of claim 13 wherein at least one of said three ligands is an antigen characteristic of Streptococcus organisms.

24. The reagent of claim 13 wherein at least one of said three ligands is an antigen characteristic of Streptococcus organisms of serogroup A.

* * * * *